(12) United States Patent
Röllin

(10) Patent No.: US 7,766,865 B2
(45) Date of Patent: Aug. 3, 2010

(54) BREAST CAP PART AND BREAST CAP FOR USING THE BREAST CAP PART

(75) Inventor: Richard Röllin, Menzingen (CH)

(73) Assignee: Medela Holding AG, Baar (CH)

( * ) Notice: Subject to any disclaimer, the term of this patent is extended or adjusted under 35 U.S.C. 154(b) by 282 days.

(21) Appl. No.: 10/587,290

(22) PCT Filed: Jan. 18, 2005

(86) PCT No.: PCT/CH2005/000024

§ 371 (c)(1),
(2), (4) Date: Jan. 4, 2008

(87) PCT Pub. No.: WO2005/070476

PCT Pub. Date: Aug. 4, 2005

(65) Prior Publication Data
US 2008/0262419 A1 Oct. 23, 2008

(30) Foreign Application Priority Data
Jan. 27, 2004 (CH) ........................... 109/04

(51) Int. Cl.
*A61M 1/06* (2006.01)
(52) U.S. Cl. ...................................................... 604/74
(58) Field of Classification Search ............ 604/74; 607/108
See application file for complete search history.

(56) References Cited

U.S. PATENT DOCUMENTS

| 4,052,981 A | 10/1977 | Bachmann |
| 4,074,222 A | 2/1978 | Kiyokawa et al. |
| 5,476,490 A | 12/1995 | Silver |
| 5,601,531 A | 2/1997 | Silver |
| 5,897,580 A | 4/1999 | Silver |
| 6,172,344 B1 | 1/2001 | Gordon et al. |
| 6,257,847 B1 | 7/2001 | Silver et al. |
| 6,261,313 B1 | 7/2001 | MacWhinnie et al. |
| 6,358,226 B1 * | 3/2002 | Ryan ........................... 604/74 |
| 6,517,513 B1 | 2/2003 | Covington et al. |
| 6,663,587 B2 | 12/2003 | Silver et al. |
| 6,676,610 B2 | 1/2004 | Morton et al. |
| 6,916,334 B2 * | 7/2005 | Noonan ..................... 607/108 |
| 7,101,350 B2 * | 9/2006 | Ytteborg ...................... 604/74 |
| 7,468,043 B2 * | 12/2008 | Morton et al. ............. 600/573 |
| 2002/0019654 A1 | 2/2002 | Ellis et al. |

(Continued)

FOREIGN PATENT DOCUMENTS

WO WO 02/17993 3/2002

*Primary Examiner*—Nicholas D Lucchesi
*Assistant Examiner*—Diva Ranade
(74) *Attorney, Agent, or Firm*—McDonnell Boehnen Hulbert & Berghoff LLP

(57) ABSTRACT

The invention relates to a breast cap part for a breast pump, which is disposed on an areola of a female breast when used. The breast cap includes a truncated base body (1) having a large rear opening (13) and a small front opening (14), the base body being embodied in order to receive a breast cap (6) in a funnel. The truncated base body (1) is at least partially made of a heat accumulating and/or heat conducting material and is heated when required. The heating does not exclusively occur when the body temperature of the female breast is transmitted. Other means for heating the breast cap part are used.

10 Claims, 2 Drawing Sheets

U.S. PATENT DOCUMENTS

| | | |
|---|---|---|
| 2002/0198489 A1 | 12/2002 | Silver |
| 2003/0073951 A1 | 4/2003 | Morton |
| 2003/0153869 A1* | 8/2003 | Ytteborg ............. 604/74 |
| 2004/0029486 A1* | 2/2004 | Greter et al. ............. 450/39 |
| 2004/0087898 A1* | 5/2004 | Weniger ............. 604/74 |
| 2006/0035081 A1 | 2/2006 | Morita et al. |
| 2006/0106334 A1* | 5/2006 | Jordan et al. ............. 604/74 |

* cited by examiner

BREAST CAP PART AND BREAST CAP FOR USING THE BREAST CAP PART

FIELD OF THE INVENTION

The invention relates to a breast cap insert for a breast pump in accordance with the preamble of patent claims 1 and 10, and to a breast cap of a breast pump for use with a breast cap insert in accordance with the preamble of patent claims 7 and 9.

BACKGROUND OF THE INVENTION

Breast pumps are known. They generally comprise a vacuum pump, a breast cap connected to the latter and placed on the areola of a human mother's breast, and a collecting container connected to the breast cap for the purpose of collecting the milk that is pumped off.

The known breast caps mainly comprise a rigid funnel, so that breast cap inserts are used to permit adaptation to different breast sizes.

These known breast cap inserts have a wide variety of forms. For example, U.S. Pat. No. 5,941,847 discloses a funnel-shaped insert with a long funnel neck. EP-A-0,237,474 discloses an insert with a cylindrical nipple attachment. This insert is made of a material that is chemically inactive in respect of water up to a temperature of 100.degree. C.

U.S. Pat. No. 5,100,406 and U.S. Pat. No. 5,885,246 describe frustoconical inserts with thicker and thinner zones intended to ensure improved stimulation of the mother's breast, in order in this way to optimize the pumping process.

WO 02/17993 discloses a breast cap insert which ensures enhanced wearing comfort. The insert comprises a frustoconical base body with an inner cone wall and an outer cone wall that form the walls of a closed chamber. The chamber is filled with air, a gas, a gel or silicone, and the inner cone wall is elastically deformable. In this way, the breast cap insert adapts optimally to the shape of the mother's breast, without exerting undesired pressure on the latter.

Moreover, U.S. Pat. No. 5,776,177 discloses a C-shaped heat pack or cold pack for therapeutic use on projecting body parts, for example on an elbow, on a shoulder or on a breast. U.S. Pat. No. 5,776,177 also discloses a breast pump in which the cap funnel is provided with a collar consisting of this heat pack or cold pack. The funnel thus surrounds the areola of the mother's breast during use, and the flange formed by the C-shaped heat pack or cold pack lies outside the areola on the breast, so that the latter is warmed or cooled. This is intended to avoid swelling and irritation of the breast.

SUMMARY OF THE INVENTION

It is an object of the invention to make available a breast cap insert for a breast pump, specifically a breast cap insert that provides a further improvement in wearing comfort and additionally has a positive influence on the pumping process.

This object is achieved by a breast cap insert having the features of patent claims 1 and 9.

A further object of the invention is to make available a breast cap of a breast pump suitable for use with improved breast cap inserts of this kind.

This object is achieved by a breast cap having the features of patent claims 10, 11 and 12.

The breast cap insert according to the invention, which breast cap insert is designed to lie on an areola of a female breast during use, comprises a frustoconical base body with a large rear opening and a small front opening, said base body being designed to be received in a funnel of a breast cap. According to the invention, the frustoconical base body is at least partly made of a heat-accumulating and/or heat-conducting material and is warmed during use. This warming does not exclusively take place through transfer of body temperature from the female breast. Instead, other means are used for warming the breast cap insert.

In a first embodiment of the invention, the insert is designed identically or similarly to that described in WO 02/17993, its chamber being provided with a filler material that has good heat-accumulating properties. Before use, this insert can be heated to a desired temperature in a water bath, in an oven, by hot air or by being placed on a heating surface. When in use, i.e. during the pumping process, it delivers its heat to the mother's breast.

In other embodiments of the invention, the insert can be heated by the breast cap during use when inserted in the breast cap, or the insert is itself provided with heating elements.

Since the breast cap insert according to the invention is heated to a desired temperature during use, the wearing comfort is enhanced. The mother does not have to place a cold insert on the sensitive breast, and instead she can choose a temperature she feels is comfortable for her.

The natural breastfeeding procedure is also taken more into account, since an infant held at the mother's breast gives off heat in the immediate area of the nipple in particular. This simulation of the heating during breastfeeding means that the mother's breast is optimally stimulated and that the pumping process is in this way optimized.

Enhanced wearing comfort and an improved pumping process can also be achieved using a breast cap insert whose conical base body is made of a foam or of a foam-like material, in particular of polyurethane foam or a polyolefin foam. This material is relatively soft and therefore pleasant to wear. In addition, it has a relatively low coefficient of thermal conduction, so that it feels warm on the skin.

Other advantageous embodiments are set forth in the dependent patent claims.

BRIEF DESCRIPTION OF THE DRAWINGS

The subject of the invention is explained below on the basis of preferred illustrative embodiments depicted in the attached drawings, in which.

DETAILED DESCRIPTION OF THE EMBODIMENTS OF THE INVENTION

Figure 1:
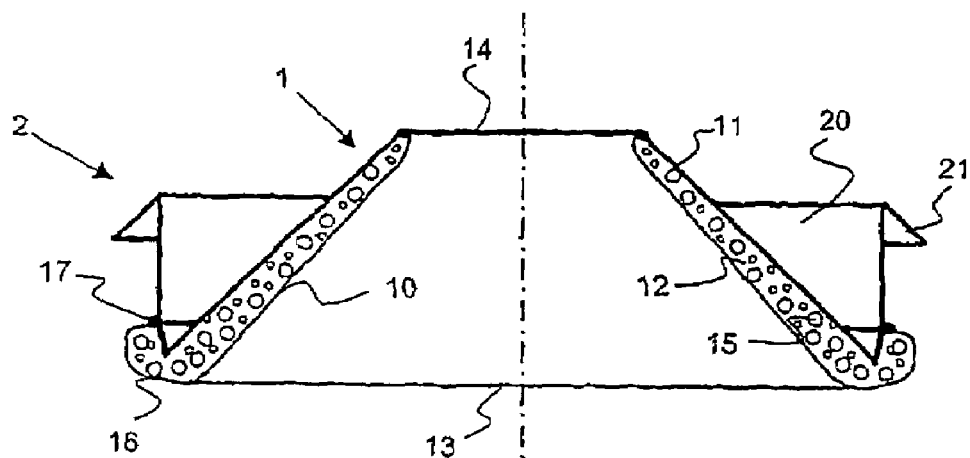
FIG. 1 shows a vertical section through a first embodiment of a breast cap insert according to the invention, with a double-walled base body.

A first embodiment of a breast cap insert according to the invention is shown in FIG. 1.

It comprises a frustoconical base body 1 with an inner cone wall 10 and an outer cone wall 11. The cone walls 10, 11 are preferably made of a plastic film or of another suitable rubber-elastic material. The film of the outer cone wall 11 preferably has a thickness of ca. 0.4 mm, and the film of the inner cone wall 10 has a thickness of ca. 0.1 to 25 mm.

At least the inner cone wall 10 is elastically deformable. Preferably, both cones walls 11 are elastically deformable. The two cones walls 10, 11 are connected to one another at a distance in such a way that they enclose a closed chamber 12. The two cone walls 10, 11 are preferably welded to one another, leaving free a large rear opening 13, directed toward the breastfeeding mother during use, and a small front opening 14. The openings 13, 14 are preferably round. The small opening 14 is used to leave free the nipple of the mother's breast.

To ensure that the weld seams do not damage or irritate the breast, the film of the inner cone wall 10, especially in the area of the large opening, is turned back over the film of the outer cone wall 11 so that a soft padding 16 is formed and the weld seam 17 is located on the outside of the insert. The padding 16 protrudes from a funnel of a breast cap during use.

To secure the insert on a breast cap of a breast pump, a peripheral collar 2 is formed integrally on the body 1 in the area of its large opening 13. This collar 2 is preferably made of a deformable film. It can be welded onto the weld seam of the two cone walls 10, 11. However, one of the two cone walls 10, 11 can also be made longer. The collar 2 is preferably V-shaped. A first branch 20 of the collar 2 rests on the funnel of the breast cap, while a second branch 21 protrudes from this and can be easily gripped by hand for the purpose of removing the insert from the cap.

A deformable filler medium 15 is present in the chamber 12. The chamber 12 is preferably filled completely by this medium 15. According to the invention, the medium 15 is a heat-accumulating and/or heat-conducting material. It is preferably a gel, in particular a medical paraffin oil or petrolatum, or a thickened liquid having such properties.

According to the invention, the insert or at least its base body 1 is warmed before or during its use. This warming can be done in a variety of ways.

For warming before use, the insert is heated to the desired temperature in a water bath, for example. The insert can also be placed in an oven or acted upon by hot air. Moreover, the insert can be placed on a heating element and heated by thermal conduction. This heating element is, for example, part of the breast pump and preferably already shaped according to the shape of the insert. For example, the heating element is formed as a frustoconical support, such that the insert can be placed on the heating element to warm it. To accelerate the warming process, a lid with a frustoconical internal shape is preferably also provided and is placed on the turned back insert, so that lid and heating element form a closed cavity for receiving the insert. The lid itself is preferably also provided with heating elements in addition to or instead of the frustoconical support.

If the insert is warmed in the manner described above, it or its filler medium is made at least partly of a material that has good heat-accumulating properties.

Figure 2:
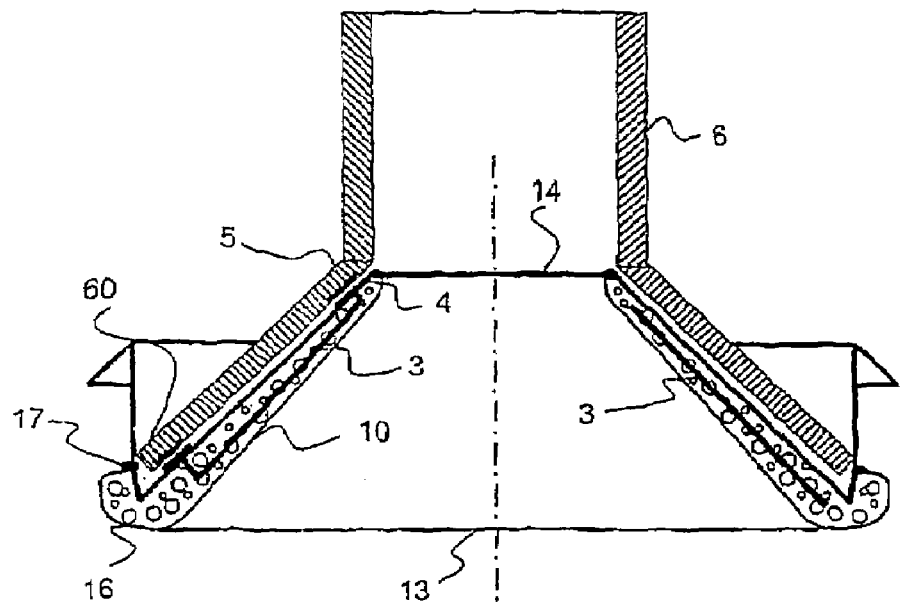
FIG. 2 shows a vertical section through a breast cap and a breast cap insert with a resistance heating element, according to a second embodiment of the invention.

In the embodiment shown in FIG. 2, the insert can be warmed before or during its use. For this purpose, at least one resistance heating element, here in the form of a resistance heating wire 3, is arranged on the base body 1. This resistance heating wire 3 is connected to electrical contact means 4, preferably contact faces, which are fitted on the outside of the insert. These contact means 4 make contact with electrical contact elements 5 which are arranged on the inner face of the breast cap 6 and which are connected via electrical lines to the breast pump. Once the insert has been fitted in the breast cap 6, the contact is closed and the resistance heating elements are heated via the current supply of the breast pump, so that the base body 1 of the insert warms up. If the insert is warmed during use of the breast pump, a good storage capacity is not absolutely necessary. In this case it is more important to have good heat conduction from the warmed base body to the mother's breast.

Figure 3:
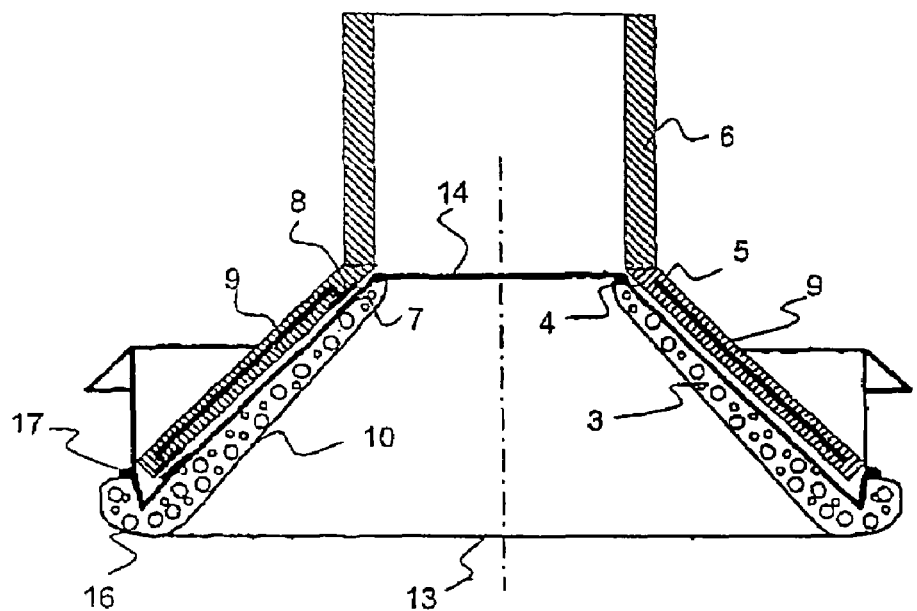
FIG. 3 shows a vertical section through a breast cap and a breast cap insert with a trigger means, according to a third embodiment of the invention.

FIG. 3 shows another illustrative embodiment. Here, the breast cap insert has trigger means 7 which make contact with or activate switch means 8 on the breast cap 6 when the insert is fitted in the cap. In this way, a heating system 9 arranged in the breast cap 6 is activated. The heating system 9 is preferably made up of resistance heating wires. The heating system 9 delivers heat to the breast cap insert by thermal radiation and conduction, so that said insert is again warmed up and conveys the heat to the breast. Examples of suitable trigger means 7 and switch means 8 are electrical contact faces, in particular metal plates, which close a current circuit. However, pin/plug connections or other suitable means can also be used for closing a current circuit and activating the heating system 9. It is also possible for the cap or another part of the breast pump to be provided with a switch for activating a heating system in the cap, without the breast cap insert requiring trigger means.

Also in the embodiment according to FIG. 3, a high coefficient of thermal conduction and/or a high heat accumulation capacity of the base body 1 is required depending on the kind of use involved.

The embodiments with a heating system integrated in the cap have the advantage that the breast cap insert, which is a disposable product, can be produced relatively inexpensively.

In the figures described above, the breast cap insert is only shown in a diagrammatic manner, particularly the interaction of the breast cap and the breast cap insert. In reality, the collar 2 is turned back around the front end of the breast cap 6 directed away from the body and also lies, in this front area of the breast cap, on the outer surface 60 of the funnel of the breast cap 6. In this way it is also possible to arrange the contact elements 5 and the switch means 8 on this outer face of the breast cap and to arrange the contact means 4 and the trigger means 7 on the inner face of the collar 2. This arrangement has the advantage that these elements and means do not come to lie between cap and breast and therefore cannot act as pressure points on the sensitive breast.

The embodiments described above are preferably configured with a double wall and comprise a chamber 12 filled with a filler material. However, they or their base bodies can also be formed in one piece from a suitably soft and deformable material. In particular, the embodiments with a heating system integrated in the breast cap insert or in the breast cap do not necessarily require a gel-filled chamber.

Figure 4:
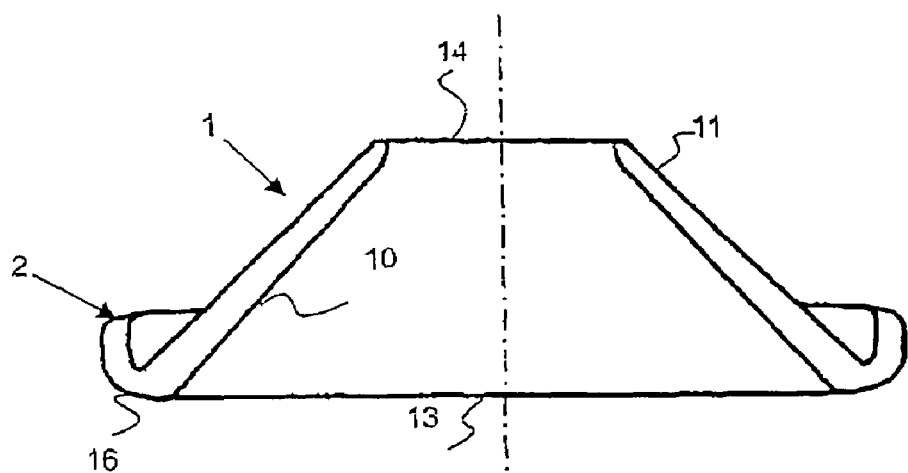
FIG. 4 shows a vertical section through a fourth embodiment of a breast cap insert according to the invention.

FIG. 4 shows a further illustrative embodiment of a breast cap insert according to the invention. The insert has essentially the same shape as has been described above. It too comprises a collar 2 which can be turned back over a front end of a breast cap in order to hold the insert in the funnel of the breast cap. However, it is produced in one piece from a relatively soft but nonetheless shape-stable foam or a suitable foam-like material, in particular polyurethane foam or a polyolefin foam.

The breast cap insert according to the invention, and the breast cap according to the invention for a breast pump, enhance comfort during use and optimize the pumping process.

The invention claimed is:

1. A breast cap insert for a breast pump, the breast cap insert being designed to overlie the areola of a female breast during use, said breast cap insert comprising a frustoconical base body with a large rear opening and a small front opening, said base body being designed to be received in a funnel of a breast cap, wherein the frustoconical base body is at least partly made of a heat-accumulating or a heat-conducting material and is warmed during use to a temperature chosen by a mother, the warming not exclusively taking place through transfer of body temperature from the female breast, and wherein said base body is provided with at least one resistance heating element, and the breast cap insert has an electrical contact communicating with the at least one resistance heating element.

2. The breast cap insert as claimed in claim 1, in which the base body has an inner cone wall and outer cone wall which form a chamber, the chamber being provided with a heat-accumulating or a heat-conducting filler medium.

3. The breast cap insert as claimed in claim 2, in which at least the inner cone wall is elastically deformable.

4. The breast cap insert as claimed in claim 2, in which the filler medium is a gel.

5. The breast cap insert as claimed in claim 1, wherein the base body is secured to the funnel of the breast cap.

6. The breast cap insert as claimed in claim 5, wherein the base body is secured to the funnel of the breast cap by a collar surrounding the large opening.

7. A breast cap of a breast pump for use with a breast cap insert as claimed in claim 1, in which the funnel of the breast cap has electrical contact elements engaging with the electrical contact of the insert.

8. A breast cap insert for a breast pump, the breast cap insert being designed to overlie at least the areola of a female breast during use, said breast cap insert comprising a frustoconical base body with a large rear opening and a small front opening, said base body being designed to be received in a funnel of a breast cap, wherein the frustoconical base body is at least partly made of a heat-accumulating or a heat-conducting material and is warmed during use to a temperature chosen by a mother, which is above-body temperature, wherein said breast cap insert is provided with a trigger for activating a heating system arranged in the funnel of the breast cap during use.

9. A breast cap of a breast pump for use with a breast cap insert as claimed in claim 8, in which the heating system for warming the insert fitted in the breast cap has a switch which is connected to the heating system and makes contact with the trigger of the insert.

10. A breast cap insert for a breast pump, the breast cap insert being designed to overlie the areola area of a female breast during use, said breast cap insert comprising a frustoconical base body with a large rear opening and a small front opening, said base body being designed to be received in a funnel of a breast cap, wherein at least the base body is made of a polyurethane foam or a polyolefin foam, which is capable of absorbing heat to raise the temperature of said base body for warming the breast in use.

* * * * *

UNITED STATES PATENT AND TRADEMARK OFFICE
CERTIFICATE OF CORRECTION

| | | |
|---|---|---|
| PATENT NO. | : 7,766,865 B2 | Page 1 of 1 |
| APPLICATION NO. | : 10/587290 | |
| DATED | : August 3, 2010 | |
| INVENTOR(S) | : Richard Rollin | |

It is certified that error appears in the above-identified patent and that said Letters Patent is hereby corrected as shown below:

In column 1, line 58, please delete the phrase "claims 1 and 9" and replace with the phrase --claims 1 and 10--.

In column 1, line 63, please delete the phrase "claims 10, 11, and 12" and replace with the phrase --claims 7 and 9--.

Signed and Sealed this

Sixteenth Day of November, 2010

David J. Kappos
*Director of the United States Patent and Trademark Office*